(12) United States Patent
Varadaraj

(10) Patent No.: US 7,117,722 B2
(45) Date of Patent: Oct. 10, 2006

(54) METHOD FOR DETERMINING VISCOSITY OF WATER-IN-OIL EMULSIONS

(75) Inventor: Ramesh Varadaraj, Flemington, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/962,688

(22) Filed: Oct. 12, 2004

(65) Prior Publication Data

US 2005/0132779 A1    Jun. 23, 2005

Related U.S. Application Data

(60) Provisional application No. 60/532,251, filed on Dec. 23, 2003.

(51) Int. Cl.
*G01N 11/00* (2006.01)
*G01N 33/26* (2006.01)
*C10G 17/00* (2006.01)

(52) U.S. Cl. .................. 73/54.01; 73/54.02; 73/53.05; 208/263; 208/265; 208/282

(58) Field of Classification Search ............... 73/53.05, 73/54.01, 54.02; 208/263, 265, 282
See application file for complete search history.

(56) References Cited

U.S. PATENT DOCUMENTS 5,820,750 A * 10/1998 Blum et al. .................. 208/263
2002/0033265 A1 * 3/2002 Varadaraj .................... 166/303

* cited by examiner

*Primary Examiner*—Daniel S. Larkin
(74) *Attorney, Agent, or Firm*—Ramesh Varadaraj; Paul E. Purwin

(57) ABSTRACT

Method to determine the viscosity of a water-in-oil emulsion that will be formed by an oil comprising organic acids when mixed with water comprising:
determining the value of the expression:

$$\eta_{(emul)} = \frac{K\eta_{(oil)} \text{TAN}^{-r}}{(1-\phi)^{2.5}}$$

wherein $\eta_{(oil)}$ is the viscosity the oil, TAN is the total acid number of the oil, $\phi$ is a number in the range of 0.1 to 0.8, $r$ is a number in the range of about 0.5 to 2, and $K$ is a number from about 1 to 20, said determined value, $\eta_{(emul)}$ being the viscosity of the water-in-oil emulsion.

The method is used to prepare water-in-oil emulsions of predetermined viscosity and to improve desalting of oils.

9 Claims, 1 Drawing Sheet

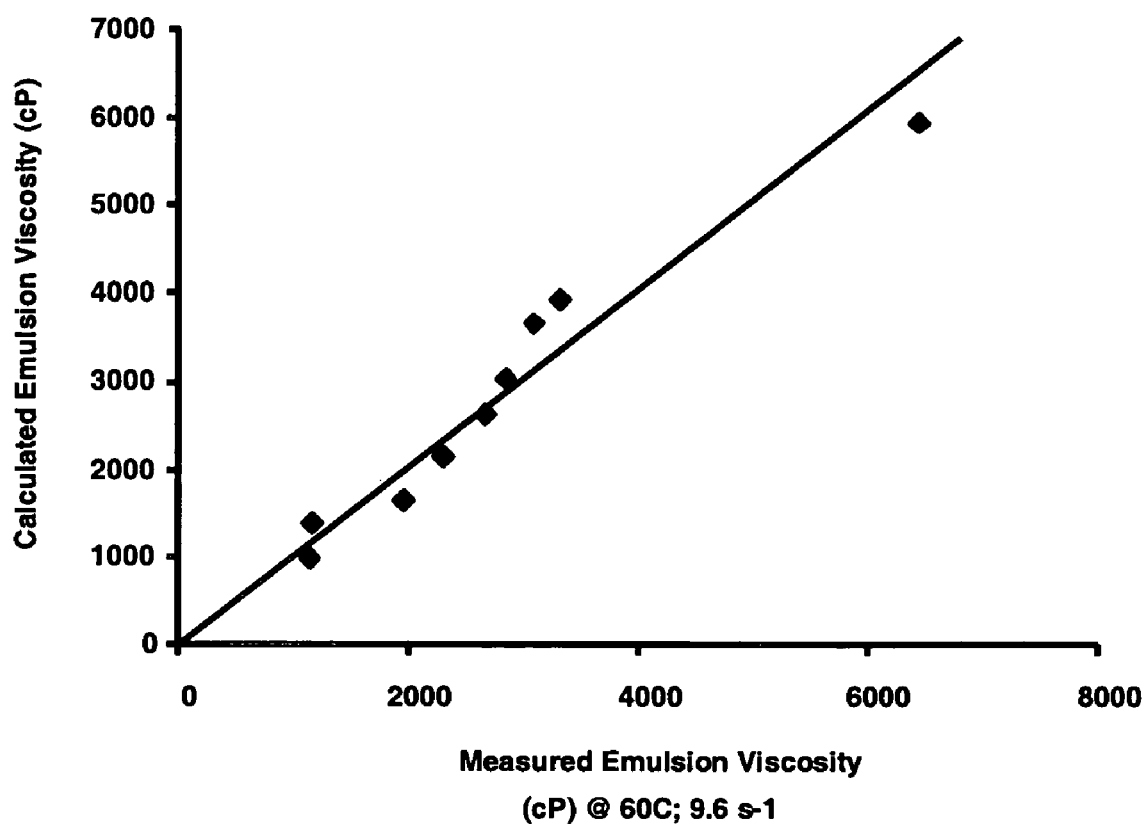

METHOD FOR DETERMINING VISCOSITY OF WATER-IN-OIL EMULSIONS

This application claims the benefit of U.S. Provisional 60/532,251 filed Dec. 23, 2003.

FIELD OF THE INVENTION

The invention relates to the viscosity of water-in-oil emulsions. More particularly the invention relates to the viscosity of water-in-oil emulsions formed from oils comprising organic acids.

BACKGROUND OF THE INVENTION

Removal of corrosive water-soluble salts, particularly chlorides of sodium and potassium from crude oil is an important processing operation in refining of crude oils. The process of desalting usually involves addition of 1 to 20 weight percent wash water to the crude oil with mixing to form a water-in-crude oil emulsion. Then, the water-in-crude oil emulsion is subjected to electrostatic demulsification or hydrocyclone treatment. Under the influence of electrostatic or centrifugal fields the dispersed water droplets coalesce and the water-in-oil emulsion is demulsified. Thereafter, the water containing water soluble salts is separated from the crude oil.

Most heavy crude oils contain asphaltenes and naphthenic acids and tend to form stable high viscosity water-in-oil emulsions. Both, the stability and the high viscosity of the water-in-oil emulsions present difficulties in demulsification. Inefficient demulsification results in inefficient dewatering and desalting of the heavy crude oils. Large volumes of a rag layer tend to form in the separator vessels and result in substantial oil loss during dewatering and desalting processes. Current methods using centrifuges, hydrocyclones and electrostatic demulsifiers require large doses of demulsifier chemicals to destabilize the water-in-oil emulsions. High emulsion viscosity requires higher than normal operation temperatures and longer residence times for desalting and/or dewatering these water-in-oil emulsions in the separator vessels. Thus, there is a continuing need for improved cost-effective methods to dewater and desalt water-in-oil emulsions especially those formed from heavy crude oils. In particular there is a need to determine the viscosity of water in-oil emulsions formed from heavy crude oils using heavy oil composition data prior to desalting and dewatering operations so that the operating conditions of the separator vessels can be adjusted prior to dewatering and desalting. There is also a need for improved methods to form low viscosity water-in-oil emulsions for a variety of applications. Such applications include low viscosity lubricant fluids and low viscosity pusher fluids for improved oil recovery. The present invention addresses these needs. In particular, hydrocarbon oils that contain asphaltenes and naphthenic acids, such as crude oils, tend to form water-in-oil emulsions with a wide range of viscosity.

SUMMARY OF THE INVENTION

Broadly stated, the present invention provides a method to determine the viscosity of a water-in-oil emulsion that will be formed by an oil comprising organic acids when mixed with water. The method comprises determining the value of the expression:

$$\eta_{(emul)} = \frac{K\eta_{(oil)}\text{TAN}^{-r}}{(1-\phi)^{2.5}}$$

wherein $\eta_{(oil)}$ is the viscosity the oil, TAN is the total acid number of the oil, $\phi$ is a number in the range of 0.1 to 0.7, r is a number in the range of about 0.5 to 2, and K is a number from about 1 to 20, said determined value, $\eta_{(emul)}$ being the viscosity of the water-in-oil emulsion.

Another embodiment of the invention comprises a method for forming a water-in-oil emulsion of predetermined viscosity by adjusting the TAN of the oil in an amount sufficient to provide the oil when mixed with water with the predetermined viscosity. The requisite TAN is determined from the expression:

$$\text{TAN}^r = \frac{K\eta_{(oil)}}{\eta_{(emul)}\{1-\phi\}^{2.5}}$$

wherein $\eta_{(oil)}$ is the viscosity the oil, TAN is the total acid number of the oil, $\phi$ is a number in the range of 0.1 to 0.7, r is a number in the range of about 0.5 to 2, K is a number from about 1 to 20 and $\eta_{(emul)}$ is the predetermined viscosity of the water-in-oil emulsion.

In yet another embodiment, the method for desalting oils by mixing an oil with water and forming a water-in-oil emulsion and thereafter demulsifying the emulsion is improved by forming a water-in-oil emulsion of predetermined viscosity by adjusting the TAN of the oil in an amount sufficient to provide the oil when mixed with water with the predetermined viscosity. The requisite TAN is determined from the expression:

$$\text{TAN}^r = \frac{K\eta_{(oil)}}{\eta_{(emul)}\{1-\phi\}^{2.5}}$$

wherein $\eta_{(oil)}$ is the viscosity the oil, TAN is the total acid number of the oil, $\phi$ is a number in the range of 0.1 to 0.7. r is a number in the range of about 0.5 to 2, K is a number from about 1 to 20 and $\eta_{(emul)}$ is the predetermined viscosity of the water-in-oil emulsion.

BRIEF DESCRIPTION OF FIGURES

The accompanying FIGURE is a plot of experimentally determined emulsion viscosity versus emulsion viscosity calculated by the method of the instant invention.

DETAILED DESCRIPTION OF THE PREFERRED EMBODIMENTS

The invention provides a method to determine for an oil comprising organic acids the viscosity of a water-in-oil emulsion that will be formed by said oil with water. The method comprises determining the value of the expression:

$$\eta_{(emul)} = \frac{K\eta_{(oil)}\text{TAN}^{-r}}{(1-\phi)^{2.5}}$$

wherein $\eta_{(oil)}$ is the viscosity the oil, TAN is the total acid number of the oil, $\phi$ is a number in the range of 0.1 to 0.8, r is a number in the range of about 0.5 to 2, and K is a number from about 1 to 20, said determined value, $\eta_{(emul)}$ being the viscosity of the water-in-oil emulsion.

The method of the invention is applicable to any oil including but not limited to crude oils, crude oil distillates, thermally treated oils and hydrocarbon oil residue obtained from crude oil distillation or mixtures thereof. The method requires knowing for any given oil its viscosity, $\eta_{(oil)}$ at a given temperature and the total acid content known as the total acid number (TAN). These values can be measured by techniques well known in the art.

The TAN of the oil is the total acid number typically expressed as an acid neutralization or acid number, which is the number of milligrams of potassium hydroxide required to neutralize 1 gram of oil. The ASTM D-664 (American Standards and Testing Method) can be used to determine the TAN of an oil. TAN can have a value in the range of 0.1 to 20. Preferably, TAN has a value in the range of about 0.1 to 10, and more preferably in the range of about 0.1 to 5.

The method also requires knowing the amount of water that will be used in forming the water-in-oil emulsion. The term $\phi$ in the expression $$\eta_{(emul)} = \frac{K\eta_{(oil)}\text{TAN}^{-r}}{(1-\phi)^{2.5}}$$

relates to the amount of water in the water-in-oil emulsion. It is the fraction of water in the emulsion and is denoted as a number between 0.01 and 0.99. For example, if the water content of the water-in-oil emulsion is 30% then $\phi$ will have a value of 0.3. Preferably, $\phi$ will take values from 0.1 to 0.8. The water in the water-in-oil emulsion is the dispersed phase in the oil continuous phase. The water is preferably dispersed as droplets in the size range of 0.05 to 400 microns diameter. More preferably in the size range of 0.05 to 100 microns diameter and even more preferably in the size range of 0.05 to 50 microns diameter.

The value of r, the exponent for TAN, can range from 0.5 to 2.0. The preferred value for r is from 0.75 to 0.95. The most preferred value for r is 0.83 when the oil is a crude oil, crude oil distillate, thermally treated oil or hydrocarbon oil residue obtained from crude oil distillation or mixtures thereof. The value of K in the expression is the proportionality constant and can vary from 1 to 20. The preferred value for K is from 1.5 to 12 and the more preferred value for K is from 4 to 8. The most preferred value for K is 5.94 when the oil is a crude oil, crude oil distillate, thermally treated oil or hydrocarbon oil residue obtained from crude oil distillation or mixtures thereof. The values of K and r can be determined for a given type of oil by generating a correlation plot. The generation of a correlation plot and determination of K and r is illustrated below for a set of hydrocarbon oils.

Five crude oils: Talco, Tulare, Miandoum, Kome, and Hoosier, three crude oil blends From Korne and Miandoum crude oils, and four thermally treated Kome crude oils, were used for illustrating the invention. For each oil the corresponding water-in-oil emulsion was made at a ratio of 60% water:40% crude oil. To 40g of the oil was added 60 g of water comprising 1 wt % sodium chloride with continuous mixing. A Silverson mixer supplied by Silverson Machines, Inc. East Longmeadow, Massachusetts was used for mixing. Mixing was conducted at 25° C. and at 400 to 600 rpm for a time required to disperse all the water into the oil. Water was added to the crude oil in aliquots spread over five additions. Viscosity of each emulsion was determined using a Brookfield viscometer at 60° C. over a shear rate range of 1.92 sec$^{-1}$ to 384 sec$^{-1}$.

Viscosity of each oil was determined using a Haake viscometer at 60° C. over a shear rate range of 1.92 sec$^{-1}$ to 384 sec$^{-1}$. The TAN for each oil was determined by the ASTM D-664 titration method. Emulsion viscosity was calculated using the Roscoe expression:

$$\eta_{calculated\ emulsion} = \eta_{oil}/(1-\phi)^{2.5}$$

where $\eta_{oil}$ is the viscosity of the oil and $\emptyset$ is the fraction of water in the emulsion.

Table-1 is a compilation of data from the above experiments. The experimentally measured viscosity ($\eta_{emulsion\ measured}$) of the emulsions deviate significantly from the values calculated ($\eta_{calculated\ emulsion}$) using the Roscoe expression. By plotting the ratio of experimentally measured emulsion viscosity to calculated emulsion viscosity using Roscoe expression:

$\{(\eta_{emulsion\ measured})/(\eta_{calculated\ emulsion})\}$ versus TAN an exponential relationship is observed. Applying curve fitting techniques known in the art of curve fitting, we obtain a value for the proportionality constant, K=5.94 and a value for the exponent, r=0.83.

The accompanying FIGURE is a plot of experimentally determined emulsion viscosity versus viscosity values calculated from the expression of the instant invention:

$$\eta_{(emul)} = \frac{5.49\eta_{(oil)}\text{TAN}^{-0.83}}{(1-\phi)^{2.5}}$$

The calculated and experimentally determined values of viscosity of the instant invention are in close agreement with each other illustrating one aspect of the invention.

TABLE 1

| Entry # | Crude Oil | Meas. Emul. Vis (cP), 9.6 s-1.60 C. | Calc. Emul. Vis (Roscoe Eqn) | TAN | Oil Vis (cP), 9.6 s-1.60 C. |
|---|---|---|---|---|---|
| 1 | Talco | 3030 | 356 | 0.7 | 36 |
| 2 | Hoosier | 5954 | 2158 | 2.3 | 218 |
| 3 | Kome | 3664 | 2099 | 5.4 | 212 |
| 4 | Miandoum | 983 | 297 | 1.7 | 30 |
| 5 | Tulare | 1370 | 1030 | 7.4 | 104 |
| 6 | Kome/Mian: 75/25 | 2621 | 1644 | 4.8 | 166 |
| 7 | Kome/Mian: 50/50 | 2129 | 198 | 3.9 | 121 |
| 8 | Kome/Mian: 25/75 | 1638 | 752 | 2.7 | 76 |
| 9 | Heat Trt #1 Kome | 3931 | 465 | 0.8 | 47 |
| 10 | Heat Trt #2 Kome | 3931 | 465 | 0.8 | 47 |
| 11 | Heat Trt #3 Kome | 3603 | 604 | 2.1 | 61 |
| 12 | Heat Trt #4 Kome | 3276 | 426 | 1.8 | 43 |

Another embodiment of the invention comprises a method for forming a water-in-oil emulsion of predetermined viscosity by adjusting the TAN of the oil in an amount sufficient to provide the oil when mixed with water with the predetermined viscosity. The requisite TAN is determined from the expression:

$$\mathrm{TAN}^r = \frac{K\eta_{(oil)}}{\eta_{(emul)}\{1-\phi\}^{2.5}}$$

wherein $\eta_{(oil)}$ is the viscosity the oil, TAN is the total acid number of the oil, $\phi$ is a number in the range of 0.1 to 0.7, r is a number in the range of about 0.5 to 2, K is a number from about 1 to 20 and $\eta_{(emul)}$ is the predetermined viscosity of the water-in-oil emulsion.

The oil viscosity $\eta_{(oil)}$ is the measured oil viscosity at a given temperature. The water content $\phi$ and emulsion viscosity are the predetermined or desired values. K and r are numbers for a given oil type. For example, for a given set of hydrocarbon crude oils K=5.94 and r=0.83. If a 40% water content is desired then $\phi$=0.4. The final desired emulsion viscosity is $\eta_{(emul)}$. The values of $\eta_{(oil)}$, $\eta_{(emul)}$, $\phi$, K and r are substituted in the expression and the TAN value calculated. The next step is to adjust the TAN value of the oil. For a given oil the TAN can be adjusted by a variety of ways by treating the oil to decrease or increase the TAN of the oil. Any treatment that decreases the TAN of the oil will result in a treated oil that will form a water-in-treated oil emulsion with a viscosity higher than the corresponding water-in-untreated oil emulsion. Similarly, any treatment that increases the TAN of the oil will result in a treated oil that will form a water-in-treated oil emulsion with a viscosity lower than the corresponding water-in-untreated oil emulsion.

Some non-limiting examples of treatments or hydrocarbon oils that can result in TAN reduction of the oil and result in formation of high viscosity water-in-treated oil emulsions are:
a) mixing low naphthenic acid containing oils with the oil,
b) thermal or electrochemical treatments of the oil under conditions where the total acid content is reduced, for example, thermal or catalytic decarboxylation,
c) chemical treatment of the oil where the naphthenic acid is chemically altered to a non-acidic form, for example, conversion of the acids to esters or ketones, and
d) any treatment that extracts or removes naphthenic acid from the oil.

Some non-limiting examples or treatments of hydrocarbon oils that can result in an increase in TAN of the oil and result in formation of low viscosity water-in-oil emulsions are:
a) adding organic acids to the oil such as petroleum naphthenic acids, and organic acids with the general structure R-COOH where R is a hydrocarbon comprising one to forty carbon atoms,
b) thermal, chemical biological or photochemical oxidation of the oil, and
c) mixing with high naphthenic acid containing oils.

In yet another embodiment, the method for desalting oils by mixing an oil with water and fanning a water-in-oil emulsion and thereafter demulsifying the emulsion is improved by forming a water-in-oil emulsion of predetermined viscosity by adjusting the TAN of the oil in an amount sufficient to provide the oil when mixed with water with the predetermined viscosity. The requisite TAN is determined from the expression:

$$\mathrm{TAN}^r = \frac{K\eta_{(oil)}}{\eta_{(emul)}\{1-\phi\}^{2.5}}$$

wherein $\eta_{(oil)}$ is the viscosity the oil, TAN is the total acid number of the oil, $\phi$ is a number in the range of 0.1 to 0.7, r is a number in the range of about 0.5 to 2, K is a number from about 1 to 20 and $\eta_{(emul)}$ is the predetermined viscosity of the water-in-oil emulsion.

The TAN of the oil to be desalted can be altered in a variety of ways as described above whereby the water-in-oil emulsion that results when the oil is mixed with water has a lower viscosity than that which would be obtained if the TAN was not altered. Such an emulsion will exhibit improved demulsification and desalting.

What is claimed is:

1. A method for desalting oils comprising:
a. determining TAN and viscosity of the oil,
b. mixing the oil with water to form a water-in-oil emulsion,
c. determining viscosity of the water-in-oil emulsion in accordance with the expression:

$$\eta_{(emul)} = \frac{K\eta_{(oil)}\mathrm{TAN}^{-r}}{(1-\phi)^{2.5}}$$

wherein $\eta_{(oil)}$ is the viscosity the oil, TAN is the total acid number of the oil, $\phi$ is a number in the range of 0.1 to 0.8, r is a number in the range of about 0.5 to 2, and K is a number from about 1 to 20, said determined value, $\eta_{(emul)}$ being the viscosity of the water-in-oil emulsion,
d. adjusting the TAN of the oil sufficiently to adjust the viscosity of the emulsion, $\eta_{(emul)}$, as determined in accordance with step c, to a predetermined value, and
e. demulsifying the emulsion.

2. The method of claim 1 wherein said oil is a crude oil, crude oil distillate, residua from crude oil distillation, thermally treated oil and mixtures thereof.

3. The method of claim 2 wherein the value of K is 5.94.

4. The method of claim 2 wherein the value of r is 0.83.

5. The method of claim 1 wherein the water-in-oil emulsion has a water content in the range of about 1 to 80 wt % based on the weight of the emulsion.

6. The method of claim 1 wherein the total acid number TAN of the oil is in the range of about 0.1 to about 20.

7. The method of claim 1 wherein said adjusting the TAN of the oil is achieved by treatment of the oil to increase or decrease the TAN of the oil.

8. The method of claim 7 wherein the treatment to decrease the TAN of the oil and increase $\eta_{(emul)}$ comprises:
a. mixing low naphthenic acid containing oils with the oil,
b. thermal or catalytic decarboxylation,
c. chemical treatment of the oil where the naphthenic acid is chemically altered to a non-acidic form,
d. or a combination thereof.

9. The method of claim 7 wherein the treatment to increase the TAN of the oil and decrease $\eta_{(emul)}$ comprise:
a. adding organic acids to the oil having the general structure R-COOH where R is a hydrocarbon comprising one to forty carbon atoms,
b. thermal, chemical, biological or photochemical oxidation of the oil,
c. mixing with high naphthenic acid containing oils,
d. or a combination thereof.

* * * * *